(12) United States Patent
Ward

(10) Patent No.: US 8,517,092 B2
(45) Date of Patent: Aug. 27, 2013

(54) METHOD FOR GROWING AND METABOLIZING MICROBES

(75) Inventor: F. Prescott Ward, Indialantic, FL (US)

(73) Assignee: MRIGlobal, Kansas City, MO (US)

( * ) Notice: Subject to any disclaimer, the term of this patent is extended or adjusted under 35 U.S.C. 154(b) by 0 days.

(21) Appl. No.: 12/884,693

(22) Filed: Sep. 17, 2010

(65) Prior Publication Data

US 2011/0061858 A1  Mar. 17, 2011

Related U.S. Application Data

(60) Provisional application No. 61/243,472, filed on Sep. 17, 2009.

(51) Int. Cl.
*E21B 43/22* (2006.01)
(52) U.S. Cl.
USPC .......................................... 166/246
(58) Field of Classification Search
USPC .................... 166/246, 264, 266, 245
See application file for complete search history.

(56) References Cited

U.S. PATENT DOCUMENTS

| | | | |
|---|---|---|---|
| 4,220,715 A | 9/1980 | Ahnell | |
| 4,475,590 A | 10/1984 | Brown | |
| 4,561,500 A | 12/1985 | Thompson et al. | |
| 4,905,761 A * | 3/1990 | Bryant | 166/246 |
| 4,971,900 A | 11/1990 | Ahnell et al. | |
| 5,297,625 A | 3/1994 | Premuzic et al. | |
| 5,316,745 A | 5/1994 | Ting et al. | |
| 5,492,828 A | 2/1996 | Premuzic et al. | |
| 5,741,971 A | 4/1998 | Lacy | |
| 5,831,721 A | 11/1998 | Alkafeef | |
| 6,758,270 B1 | 7/2004 | Sunde et al. | |
| 7,074,364 B2 | 7/2006 | Jähn et al. | |
| 7,461,547 B2 * | 12/2008 | Terabayashi et al. | 73/152.55 |
| 7,484,560 B2 | 2/2009 | Lal et al. | |
| 2006/0060350 A1* | 3/2006 | Hlatki et al. | 166/244.1 |
| 2006/0263869 A1* | 11/2006 | Evans | 435/262.5 |
| 2007/0092930 A1* | 4/2007 | Lal et al. | 435/41 |
| 2007/0181300 A1* | 8/2007 | Busche et al. | 166/246 |
| 2009/0117633 A1 | 5/2009 | Bradley et al. | |
| 2009/0308598 A1* | 12/2009 | Gardes | 166/246 |

OTHER PUBLICATIONS

Dr. Paul Evans and Dr. Braden Dunsmore, Reservoir Simulation of Sulfate-Reducing Bacteria Activity in the Deep Sub-Surface, Corrosion NACExpo 2006, pp. 1-17, Paper No. 06664, NACE International, USA.
Steven L. Bryant and Thomas P. Lockhart, Reservoir Engineering Analysis of Microbial Enhanced Oil Recovery, 2000 SPE Annual Technical Conference and Exhibition, Oct. 1-4, 2000, pp. 741-756, SPE 63229, Society of Petroleum Engineers Inc., USA.
Murray R. Gray, Anthony Yeung, Julia M. Foght and Harvey W. Yarranton, Potential Microbial Enhanced Oil Recovery Processes: A Critical Analysis, 2008 SPE Annual Technical Conference and Exhibition, Sep. 21-24, 2008, pp. 1-25, SPE 114676, Society of Petroleum Engineers, USA.
James O. Stephens, Lewis R. Brown and Alex A. Vadie, The Utilization of the Microflora Indigenous to and Present in Oil-Bearing Formations to Selectively Plug the More Porous Zones Thereby Increasing Oil Recovery During Waterflooding, Contractor Report, Jan. 1998, DOE Contractor Report No. DE-FC22-94BC14962-15.
L.R. Brown and A.A. Vadie, Slowing Production Decline and Extending the Economic Life of an Oil Field: New MEOR Technology, 2000 SPE/DOE Improved Oil Recovery Symposium, Apr. 3-5, 2000, pp. 1-16, SPE 59306, Society of Petroleum Engineers Inc., USA.
Bacterial Profile Modification, Porous Media Research Group, University of Michigan, http://sitemaker.umich.edu/sfogler/bacterial_profile_modification.
Saikrishna Maudgalya, Roy M. Knapp, Michael J. McInerney, Microbial Enhanced-Oil-Recovery Technologies: A Review of the Past, Present, and Future, 2007 SPE Production and Operations Symposium, Mar. 31-Apr. 3, 2007, pp. 1-11, SPE 106978, Society of Petroleum Engineers, USA.

* cited by examiner

*Primary Examiner* — Shane Bomar
*Assistant Examiner* — Silvana Runyan
(74) *Attorney, Agent, or Firm* — Husch Blackwell LLP

(57) ABSTRACT

The method hereof is for releasing trapped oil in reservoirs and includes identifying a reservoir, obtaining a microbial community sample of the reservoir, maintaining the sample under high temperature and high pressure conditions that mimic natural conditions of the reservoir, growing the sample on at least one substrate, determining a targeted treatment regime for the reservoir based on the positive growth of the sample on the substrate, injecting the reservoir with the targeted substrate to release trapped oil in the reservoir, monitoring the reservoir, and extracting the oil from the reservoir.

18 Claims, No Drawings

METHOD FOR GROWING AND METABOLIZING MICROBES

CROSS-REFERENCE TO RELATED APPLICATIONS

This application is a non-provisional of and claims priority to U.S. Provisional Patent Application Ser. No. 61/243,472, filed Sep. 17, 2009, which document is hereby incorporated by reference herein to the extent permitted by law.

BACKGROUND OF THE INVENTION

Approximately sixty-five percent of all the oil discovered remains trapped underground in reservoirs following primary production (natural reservoir pressure) and secondary production (water or gas flood). Microbial enhanced oil recovery ("MEOR") holds considerable promise for recovering a significant proportion of trapped global oil reserves.

Conventional MEOR is an empirical process whereby inexpensive nutrients are pumped into an oil reservoir to stimulate growth of indigenous and dormant microorganisms. In theory, the rejuvenated microbial community produces environmentally friendly biometabolites such as gases, acids, solvents, and surfactants that release trapped oil and/or biomass and polymers that plug water channels thereby diverting subsequent water or gas floods into oil bearing zones.

Conventional MEOR has been employed for decades and has been moderately successful but, frequently, the results have been disappointing. A typical MEOR approach is to pump molasses or agricultural fertilizer into a watered-out reservoir and hope for the best. This hit-or-miss approach is not based on scientific principles and any positive, negative, or damaging results remain unexplained. In some cases, undesirable bio-metabolites such as hydrogen sulfide have caused irreversible reservoir damage, equipment corrosion, and health threats.

There are many applications of MEOR, but none of them include prior metabolic characterization of microbial communities that inhabit oil reservoirs. According to some culture-based and genetic evidence, microbial communities are markedly different among oil reservoirs depending on rock type, temperature, depth, and various other factors. Therefore, blindly injecting nutrients into an oil reservoir and hoping for beneficial results is an uncertain and potentially damaging process. Pumping the same nutrient into several reservoirs and expecting similar results is unscientific and unreasonable. There is no way currently to predict what bio-metabolic response, if any, can be expected in a given oil reservoir when nutrients are injected. Therefore, it would be beneficial to have a method for growing reservoir microorganisms in a controlled and scientific way.

Targeted, scientifically-based MEOR treatments could be devised for individual oil reservoirs if one knew the likely metabolic response of the microbial community to an infusion of nutrients. Then one would need to stimulate the desirable microbes and suppress the undesirable ones, for example, sulfate-reducing bacteria responsible for souring oil. To do this in a scientific fashion, one has to know what species of bacteria live in a given reservoir, what the actions of the microbial community in a given reservoir to nutrient infusions, what bioproducts they are capable of producing, and exactly what nutrients and co-factors they need to grow at optimum rates. However, most reservoir microbes die when brought to the surface in a sampler, when those microbes are exposed to air, low temperature, low pressure, and a variety of other stressors. Few, if any, indigenous microbial species survive when hoisted to the surface. Therefore, conventional laboratory culture of oil-reservoir microorganisms in Petri dishes or in flasks of liquid growth media at room temperature is not feasible.

The basic goals of MEOR are: (1) to stimulate desirable reservoir microbes, for example, those that produce useful quantities of oil-releasing or channel-plugging materials; and (2) to suppress undesirable ones, for example, sulfate-reducing bacteria responsible for souring oil, corroding pipes and equipment, and that pose a toxic hazard to workers. To do this in a scientific and predictive fashion, one must know what bio-metabolites reservoir microbes are capable of producing, and exactly what nutrients, supplements, and co-factors they need to grow and produce specific bio-metabolites at optimum rates. However, culturing reservoir microorganisms in the laboratory to elucidate microbial community metabolism is unsatisfactory because ninety-nine percent or more die when brought to the surface because of the sudden decreases in pressure and temperature and the exposure to oxygen. Therefore, it would be beneficial to have a method for growing reservoir microorganisms under anaerobic conditions and under reservoir conditions of high temperature and high pressure.

SUMMARY OF THE INVENTION

The present invention is generally directed to a method for releasing trapped oil in reservoirs. The method hereof includes identifying a reservoir, obtaining a microbial community sample of the reservoir, maintaining the sample under high temperature and high pressure ("HTHP") conditions that mimic natural conditions of the reservoir, growing the sample on at least one substrate, determining a targeted treatment regime for the reservoir based on the positive growth of the sample on the substrate, injecting the reservoir with the targeted substrate to release trapped oil in the reservoir, monitoring the reservoir, and extracting the oil from the reservoir.

Since reservoir microbes exist under conditions of high temperature and high pressure in an anoxic and usually hypersaline environment, when sampled and brought to the surface, exposure to oxygen, low temperatures, low pressures, and lower salinity kills virtually all of the microbes. If one were able to culture them in different nutrient growth media under reservoir conditions, i.e., in a HTHP chamber, accurate measurements of metabolic by-products could be made.

Under HTHP culture, the by-products of microbes from a specific oil reservoir could be identified and predictions of growth and metabolism of the microbial consortium in the presence of a given nutrient mix could be obtained. By culturing the consortium in a number of nutrient growth media and chemically and physically measuring acids, gases, solvents, surfactants, biomass, and polymers produced, predictions could be made about specific metabolic by-products to be expected in a given oil reservoir when injected with a specific nutrient medium.

If, for example, bacterial biomass and polymers are needed to block water channels, if acid production is required to dissolve carbonate rock, if gas production is needed to repressurize the reservoir, and if nitrates are needed to suppress sulfate-reducing (oil-souring), bacteria, a treatment regime (perhaps sequential) could be devised for a specific reservoir based on the HTHP chamber culture results.

Other and further objects of the invention, together with the features of novelty appurtenant thereto, will appear in the course of the following description.

DETAILED DESCRIPTION OF THE INVENTION

There is provided herein an integrated method that significantly enhances the recovery of crude oil. The method of the present invention generally includes: (a) growing reservoir microorganisms ex situ in a variety of growth media under high temperature/high pressure ("HTHP") conditions that mimic reservoir conditions; (b) characterizing their metabolic byproducts; and (c) injecting a tailored nutrient medium into the reservoir that releases trapped oil via a variety of potential mechanisms.

The method of this invention exploits a novel application of MEOR. Specifically, the method of the present invention is a process whereby living microorganisms are obtained from oil reservoirs, are maintained at bottom hole temperatures and pressures, and are grown on different nutrient substrates in a high temperature/high pressure growth chamber. Microbial aqueous and gaseous metabolic by-products are measured by chemical and physical assays during and following the microbial growth phase and the results are used to develop specific reservoir treatment regimes with nutrients to stimulate desirable microbes, to suppress undesirable microbes, and to insure maximum production of microbial metabolic by-products that stimulate enhanced production of trapped oil. Essentially, reservoir microbes are cultured under reservoir conditions, the microbes' metabolic by-products are measured, and specific treatment regimes are developed for individual reservoirs to release trapped oil.

During the productive life of a typical oil well, the first ten percent of oil flows spontaneously to the surface because of underground pressure in the reservoir. This process is called primary production. Another twenty-five percent of the original oil in place ("OOIP") can usually be produced by secondary treatment of the reservoir. This typically involves injecting the reservoir with water under high pressure, forcing the oil ahead of the waterflood from an injector well to producer wells. However, water usually finds the path of least resistance through the rock substrate of the reservoir, and eventually water channels are formed directly from the injector well to producer wells. The amount of water appearing in the oil at the producer well is called the "water cut." Oil wells are usually capped and abandoned when water cuts exceed ninety to ninety-five percent, leaving most of the OOIP behind. The amount of trapped oil in the United States alone is estimated at 377 billion barrels.

Light, sweet crude oil reservoirs that are not too hot, too saline, or under too much pressure usually host a diverse community of microorganisms. The majority of these live at the oil-water interface (the residual oil zone or "ROZ"), and are basically in a state of suspended animation, having used up available nutrients over time and having produced growth-limiting metabolic wastes. An infusion of proper nutrients stimulates these microorganisms to grow. Table 1 hereinbelow illustrates a variety of products potentially useful in oil recovery and the typical effect those products have.

TABLE 1

| Bioproduct | Effect |
| --- | --- |
| Acids | Modification of reservoir rock |
| | Improved porosity and permeability |
| | Reaction with calcareous rocks a $CO_2$ production |
| Biomass | Selective or nonselective plugging |
| | Emulsification via adherence to hydrocarbons |
| | Modification of solid surfaces (biofilms) |
| | Degradation or alteration of oil |

TABLE 1-continued

| Bioproduct | Effect |
| --- | --- |
| Gases | Reduction of oil viscosity and oil pour point |
| | Desulfurization of oil |
| | Reservoir repressurization |
| | Oil swelling |
| | Viscosity reduction of oil |
| | Increased permeability ($CO_2$ solubilization of carbonate rocks) |
| Solvents | Reduce oil viscosity |
| Surfactants | Lowered interfacial tension |
| | Emulsification |
| Polymers | Mobility control |
| | Selective or non-selective plugging |

In one embodiment, the acids may be, but are not limited to, formic acid, acetic acid or valeric acid. In another embodiment, the gases may be, but are not limited to, carbon dioxide, methane, hydrogen sulfide, or hydrogen. In one embodiment, the solvents are primarily alcohols including, but not limited to, methanol, ethanol, propanol, isobutanol, and n-butanol. In another embodiment, the solvents are formaldehyde and acetone. In yet another embodiment, the solvents are aldehydes or ketones. In another embodiment, surfactants may be, but are not limited to, anionic compounds such as, for example, carboxylic acids; cationic compounds such as, for example, amines and heterocyclic compounds; amphoteric compounds such as, for example, amino acids and peptides; non-ionic compounds such as, for example, esters; and polyanionic lipids. In yet another embodiment, the polymers may be, but are not limited to, proteins and polysaccharides.

One embodiment of the method of the present invention provides an innovative method (i.e. anaerobic culture of microbes in reservoir fluids at subsurface conditions of temperature and pressure) to predict precisely what bio-metabolites will be produced in a targeted reservoir from treatment with various nutrient media. Based on these results and a review of the geology of the reservoir, a precise nutrient-medium formulation is devised and injected into the reservoir in optimum quantities to (a) plug watered-out channels, (b) to induce maximum production of other desirable biometabolites, and/or (c) to suppress growth and metabolism of undesirable microbes, especially those that produce hydrogen sulfide and sour oil. At least one result is the enhanced recovery of oil. An objective of the present invention is to increase the amount of oil ultimately produced above and beyond what would have been recovered using other treatments. This depends mainly on increased displacement of oil and/or improved volumetric efficiency of flooding techniques.

A reservoir is screened to determine if the reservoir is a candidate for use with the MEOR method of the present invention. Generally, indicators that a reservoir is a good candidate for use with the MEOR method of the present invention include, but are not limited to, salinity (NaCl content) of the formation water less than about 10% wt/vol; temperature less than 167-180° F.; depth of reservoir less than 8,000 feet; presence of trace elements As, Se, Ni, and Hg, less than 10-15 ppm. Permeability greater than approximately 50 mD to 75 mD; oil gravity greater than 15°-18° API; residual oil saturation greater than 25%; and/or pH between 4 and 9. Another indicator is that the concentrations of cations and anions at certain levels might interfere with microbial systems. Those cations and anions and their respective concentrations are approximately lithium 400 mg/l, barium 670 mg/l, boron 450 mg/l, bromine 6,000 mg/l, and iodine 1,400 mg/l.

Once biometabolities are elucidated via HTHP growth in the laboratory, a specific treatment regime would be developed for that reservoir. In one embodiment the treatment regime includes, but is not limited to, (1) developing an ideal formulation of nutrients, salts, growth factors, and suppressants; (2) injecting nutrients with initial waterflooding or waiting until later in the cycle; (3) injecting nutrients following fishbone drilling to reach out-of-the-way pockets of oil; (4) sequential injections (e.g., first to create biomass to plug thief, i.e., watered-out, zones, then nutrients to stimulate oil production or to channel $CO_2$ in an enhanced miscible $CO_2$ flood).

Some advantages of targeted MEOR over other previous recovery techniques are: (a) potential low costs (chemical tertiary methods such as polymer floods, surfactant floods, and others are expensive); (b) multiple mechanisms working simultaneously thereby enhancing effectiveness; (c) environmentally benign; (d) exploiting indigenous reservoir microorganisms requires only nutrient infusions similar to conventional waterfloods; (e) ability to complement and enhance selected secondary and tertiary recovery techniques including waterfloods and miscible $CO_2$ floods; and (f) prior characterization of reservoir response assures predictable and reliable MEOR results.

In one embodiment, once a target reservoir is selected, bottomhole samples are obtained, and the samples are maintained at reservoir temperatures and pressures during sampling, during transport to the laboratory, and during culture. Reservoir microbes are grown in a series of candidate nutrient media in HTHP anaerobic chambers that mimic reservoir temperature and pressure, i.e., reservoir simulators. By measuring biomass and by chemically analyzing bio-metabolites produced in the laboratory, one obtains accurate data to guide nutrient selection, concentration, and time for a targeted reservoir, thereby insuring maximum release of trapped oil and mitigating risk of reservoir damage.

A conventional industry PVT-type sampler may be used to obtain bottomhole samples, usually bringing two each 600-ml fluid samples to the surface. The reservoir samples are obtained from the oil/water interface (residual oil zone). Additional samples can be obtained if required. The bottomhole temperature and pressure are measured by the sampler itself or by a separate probe. Pressure in the canisters is maintained at bottomhole pressure by hydraulics or nitrogen injection as canisters are retrieved to the surface. Bottomhole samplers are manufactured by a variety of different oilfield service companies, and reservoir sampling support can be contracted.

"Slickline" sampling can retrieve canisters at 200 feet/minute. Using this sampling scheme, pressure is maintained, but temperature is not during ascent of the sampler up the well casing. However, sample transit via slickline from 4,000 feet is only 20 minutes, the sampling canisters provide good insulation, and subsurface microbes are probably not as susceptible to a temperature drop of a few degrees for a short time as they would be to a precipitous drop in pressure. Samples are transferred under pressure to sample-transport canisters, and transport canisters containing pressure-compensated samples are placed into a portable oven to maintain bottomhole temperature during transport to the laboratory.

Prior to transfer to HTHP growth chambers, reservoir samples are stored in an oven to maintain reservoir temperature. Reservoir bottomhole pressure is maintained inside the sample bottles, i.e., they are not opened prior to fluid transfer.

In order to culture reservoir microorganisms under reservoir conditions, any of several HTHP growth chambers are suitable. These chambers are used for growing reservoir microbial consortia in various growth media, including modifications of in situ growth chambers designed for studying deep-sea hydrothermal vents. In one embodiment, reservoir simulator is used, and it provides for transfer of samples under pressure, for growth and metabolism under reservoir conditions, and for periodic monitoring and analysis of headspace gas, real-time monitoring of pH, and periodic removal of liquids for physical (e.g. biomass) and chemical analyses. In addition, a piston arrangement allows for pressure compensation in the upper growth chamber as metabolic gases are liberated during microbial growth. Growth chambers are usually assembled in a manifold array to provide for serial dilutions of reservoir oil/water inoculums into a selected nutrient medium if required, or to provide for inoculations into several types of nutrient media. Bottomhole reservoir sample bottles containing remaining reservoir fluids are maintained at reservoir temperature and pressure between inoculations.

One embodiment and a non-limiting illustrative example of the method of the present invention is outlined below and includes the following steps: (1) An oil company identifies and characterizes light, sweet crude oil reservoir that matches preliminary MEOR screening criteria, as disclosed herein. (2) A contracted petroleum laboratory conducts conventional PVT fluid-property and other analyses on sample of retrieved oil (these data are probably already available). (3) An oil company obtains two 600-ml reservoir samples from oil/water interface (residual oil zone or ROZ). Both canisters are maintained at bottomhole pressure by nitrogen injection as canisters are retrieved to the surface. "Slickline" sampling can retrieve canisters at 200 feet/minute. (4) Canisters containing pressure-compensated samples are placed into "pizza oven" device for transport. Oil-service companies will be contacted to determine if canisters can be insulated to prevent significant temperature drop during transit from bottomhole up the casing to the surface. (5) One canister is placed into high temperature/high pressure (HTHP) robotic chamber for subsequent opening, inoculation, and microbial growth on various substrates (specific protocol to be determined). (6) The sample from the second canister is split. Approximately one-half is used for room-temperature culture attempts for indigenous microbes that will survive at ambient temperature and pressure. The other one-half is for archiving for subsequent metagenomic sequencing and/or culturing of desirable microorganisms. (7) Growth and metabolic by-product studies are conducted of bottomhole microbial consortium in various liquid growth media including molasses, nitrogen/phosphate fertilizers, and various treatment grades of industrial wastes such as paper/pulp, sugar beet, brewery, and feedlot. (8) The growth of microbial consortia in various types are assessed and dilutions of growth media by measuring (a) change in turbidity of growth medium, (b) numbers of microbes per ml (i.e., biomass), (c) volume of headspace gases produced, and (d) other measures of growth. (9) Samples of headspace gases and liquid culture medium are obtained for (a) chemical and volumetric analyses of headspace gases and (b) chemical nature of metabolic byproducts in the growth medium from microbial growth such as pH change, surfactants produced, polymers produced, and solvents produced. Alternatively, a battery of petroleum-lab screening tests in-house for "black-box" efficacy studies of fermented liquid media in releasing trapped oil may be used. These tests could include Berea cores and sand packs, surfactant break tests, and many others.

Based on measurements of microbial growth, samples from media dilutions exhibiting significant growth will be gathered and will be filtered and frozen for subsequent metagenomic analysis and for subsequent growth experiments at ambient temperature and pressure.

Fundamental data on reservoir fluids should be available from the well operator, e.g. PVT, API gravity, and other fluids data, as well as reservoir characteristics such as depth, porosity, permeability, residual oil saturation, API, water cut, and other information. Raw reservoir samples are analyzed in the laboratory for pH, biomass, and dissolved gases. In addition, chemical analyses are used to characterize oil samples as described in a chemistry discussion below.

Growth chambers are loaded with selected sterilized nutrient media at ambient temperature and pressure, and then the chambers are closed, charged with nitrogen or inert gas, and brought up to reservoir temperature and pressure. A tubular connection with pressure gauge enables transfer of a portion of reservoir fluid (inoculum) to the loaded HTHP growth chamber. During transfer of reservoir fluids, the chamber pressure is maintained at slightly less than the reservoir sample bottle to provide for metered fluid flow into the growth chamber that is not too turbulent, but is sufficiently turbulent to mix reservoir fluids and nutrient media thoroughly.

Many types of growth media are suitable for use including those typically used in empirical MEOR applications in the field. Conventional MEOR solutions include but are not limited to: molasses (an inexpensive carbon source with micronutrients that is commonly used in MEOR), 0.5% aqueous solution (vol/vol) more or less; augmented molasses: 0.5% molasses, 0.15% KNO3 (w/v), and 0.05% Na3PO4 (w/v), or variations thereof; or an aqueous solution of fertilizer: 0.25% KNO3 (w/v), and 0.05% NaH2PO4 (w/v), or variations thereof.

Many other types, concentrations, and mixtures of growth media are suitable for trials in the HTHP growth chambers. Regional industrial waste streams are evaluated to determine their suitability as potential nutrient media for MEOR. The fundamental appeal of such a "green" approach is that local waste streams could be diverted to productive and very profitable use for enhanced oil recovery. Because of regulatory requirements, many industrial waste streams have already been characterized by the supplier, and these chemical data sheets are used as background. Candidate aqueous wastes include those from breweries, food processing plants, sugar (beet and cane) refineries, pulp and paper manufacture, animal feedlots, treated municipal wastes, and many others. Industrial wastes are generally pre-filtered to remove suspended solids. Aliquots of nutrient media formulations and waste streams are analyzed chemically as described below before inoculation and incubation in HTHP growth chambers.

Typically, ninety milliliters each of MEOR nutrient solutions and industrial waste streams are loaded into separate HTHP chambers under ambient pressure, and the vessels are then charged with inert gas and pressurized. Ten milliliters of reservoir fluids from a single well are then added to each of the HTHP growth chambers under reservoir pressure, i.e. a 10% inoculum. Larger or smaller HTHP growth chambers can be used and inoculum ratios can be modified depending on requirements and growth responses.

During incubation, growth-chamber pressure is maintained at in situ reservoir pressure by hydraulic or electrical (screw) manipulation of a piston. Growth chambers are immersed in a water bath or are subject to an alternative heating method to maintain reservoir temperature. The entire apparatus is generally moved to a fume hood for containment. All chamber sensors can be connected to a control computer for process pH, gas-generation, and other monitoring and data acquisition.

Measurements of acid, gas, and biomass production is disclosed herein. Typical incubations are expected to take approximately 2-6 weeks each, and the end point is determined by cessation of acid and gas production. The volume and composition of metabolic off gases and pH of the nutrient medium are analyzed periodically in samples removed from the growth chamber to obtain gas-generation (via gas chromatograph) and acid-generation (via pH meter) curves for each reservoir-nutrient combination. Sensors can be incorporated into the construction of the HTHP growth chamber to monitor pH, pressure, gases, and other parameters and constituents remotely and in real time. Biomass is calculated during and at the end of incubation by cell count, turbidity, filtering and weighing, and/or other measurements to obtain microbial growth curves.

Following incubation, liquid samples are transferred to a chemical laboratory for analysis. Chambers are cleaned and sterilized using acceptable methods. The growth chambers can be disassembled, cleaned with a solvent to remove hydrocarbon residues, and then autoclave-sterilized at 121° C. or equivalent.

Chemical analyses of reservoir fluids and growth media are disclosed herein. Representative samples of reservoir fluids, uninoculated nutrient solutions/suspensions, and growth media following incubation from microbial reactions are analyzed chemically. As described below, the easiest and probably most profitable application of MEOR is plugging of water channels (fingers or "thief zones") in watered-out reservoirs via biomass and/or bio-polymer produced by nutrient-stimulated microbes in situ. For that reason, a high priority is given initially to developing, modifying, refining, and applying simple, straightforward measurement techniques for production of biomass and bio-polymers in reacted HTHP chamber samples.

Analytical data from chemical analyses would be difficult to interpret except in the context of changes observed in samples before and after microbiological action. For example, a nutrient source that is relatively high in sulfur content could produce an undesirable outcome from in situ microbial activity in a reservoir versus a source that is lower in sulfur. Also, some of the target microbial bio-metabolites might already exist in the reservoir fluids, and could not necessarily be shown to result solely from the laboratory incubation process. Chemistry data from the unreacted reservoir fluid and the uninoculated nutrient solutions are therefore necessary to interpret the results of the tests.

Representative samples from each source of reservoir fluid employed for HTHP growth are chemically analyzed before inoculation. These samples include water or other residual materials used in previous recovery efforts from the well(s), and it is assumed that samples contain both aqueous and non-aqueous phases. While the total volume and proportion of aqueous and non-aqueous phases vary from reservoir to reservoir, standard methods for sample preparation are utilized. These include centrifugation, filtration, and fractionation, where possible.

Representative samples of each type of nutrient source are analyzed by methods selected from those outlined below. These differ from those used to analyze the control reservoir fluid and the organic phase of the incubated media, and focus on certain nutrients and incidental constituents, such as proteins, peptides, alcohols, organic acids, sugars, N, P, K, Na, and S. Any samples that are transferred between laboratories are shipped through commercial means under refrigeration in order to minimize ongoing microbiological activity during storage and transit.

The incubated nutrient media from tests often requires additional preparation and pre-separation of phases prior to chemical analyses. The methods used for these samples are designed to obtain useful data from any separable organic and aqueous phases over the full range of applicable analytes.

The analyses selected for each of the matrices listed are based on the types of data needed to evaluate the results of media testing, including diagnostic differences between incubation runs and nutrient mixtures used. Most analyses follow specific pre-separations or other preparation steps. The target analytes may include but not be limited to: petroleum constituents of different classes, molecular weight, polarity, and volatility (analyses focuses on profiles, peak patterns, and relative differences between samples, rather than specific identification or quantification of individual constituents); surfactants (e.g., carboxylic acids, amines, amino acids, peptides, esters); solvents (lower molecular weight constituents that would dilute and decrease viscosity of oil, e.g., alcohols, ketones, and aldehydes); polysaccharides (could be introduced in the nutrient mixture, or produced as metabolites and capsular polysaccharides of bacteria in the incubated media); proteins (include soluble proteins and membrane proteins, possibly originating in the nutrient mixtures or from microbial growth); organic acids (survey of lower molecular weight organic acids, e.g., formic, acetic, and valeric); and/or specific mineral nutrients and inorganic cations (elemental analysis of N, P, K, Na, S).

Methods generally selected from, but not limited to, the following are used in analysis of samples for the types of analytes listed above. Chemical analyses provide sufficient data on types and quantities of analytes produced to make informed decisions on what nutrient medium produces best bio-metabolite results for the reservoir in question. All work is performed according to accepted standards of documentation and quality assurance. The final selection of methods is partially dependent on the kind, volume, and number of samples.

The qualitative analysis of both known and unknown non-volatile chemicals can be performed using liquid chromatography/mass spectrometry (LC/MS). Samples such as the organic and aqueous phases of unreacted reservoir fluid, unreacted nutrient solutions, and organic and aqueous phases of incubated media are prepared for analysis using suitable pre-separation and extraction methods, and are then introduced into the LC/MS system. The system allows for the chromatographic separation of chemicals in the sample such as acids, solvents and surfactants prior to introduction into the mass spectrometer. Because the chemicals of interest can be somewhat separated prior to introduction into the mass spectrometer, a total ion fingerprint can be obtained by full scan analysis with the mass spectrometer.

Identification information from the fingerprint region can be obtained from individual peaks in the chromatogram to determine the number of compounds in each peak as well as information on potential molecular ions of individual chemicals. Additional testing, if warranted, includes product ion scans (LC-MS/MS) of each separated chemical in which the molecular ion is isolated and fragmented (utilizing collision induced dissociation). The product ions (fragments), as well as the calculated neutral losses, are then used to propose structures or chemical classes for the constituents extracted from the original samples.

Gas chromatography/mass spectrometry (GC/MS) is an additional tool that is used, as appropriate, in the analysis of the various samples. It is particularly well-suited for the identification of petroleum constituents such as alkanes, alefins, naphthenes, and aromatics, as well as solvents that may be present in these samples. Initially, full-scan GC/MS is used to analyze samples that have been suitably extracted and prepared. As in the LC/MS analysis, these data are used to obtain an overall picture of a sample (e.g. number and types of compounds present), which can then be followed by more targeted analyses. Mass spectrometry techniques and instrumentation for in-depth analysis of samples include, but are not limited to the following samples outlined below.

A High Resolution MS (e.g. Waters AutoSpec Premier) instrument capable of high R>10,000 amu mass spectral resolution to improve detection confidence in the presence of interfering ions.

Heart-Cut GC-GC/MS systems consisting of gas chromatographs coupled with a mass spectral detector and equipped with heart-cutting systems offering excellent matrix rejection through the selective "cutting" of discrete effluent from the first C column and placement on the second column.

Multi-Dimensional systems, e.g. GC×GC-TOFMS (Leco GC×GC-TOFMS, Pegasus 4D) capable of performing multi-dimensional GC separations through thermal modulation GC×GC. Such separations provide an alternative, multi-dimensional separation versus heart-cutting through an advanced thermal modulation system and are increasingly being used for the analysis of petroleum samples. The technique enables the increased separation of alkanes, olefins, naphthenes, and aromatics with limited sample preparation making it well suited to unknown analyses.

A variety of detectors, other than mass spectrometry, can also be used for coupling with gas chromatography for sample analysis, including Pulse Flame Photometric Detectors, Flame Ionization Detectors, and Electron Capture Detectors.

Due to partition of some analytes between aqueous and non-aqueous phases, some of the same materials can be observed by both GC/MS and LS/MS depending on the pre-separation and preparation methods selected.

Proteins and other larger molecular compounds are qualitatively analyzed using Matrix-Assisted Laser Desorption/Ionization Time-of-Flight Mass Spectrometry (MALDI-TOF MS) or LC/MS/MS technologies. Samples are processed using suitable extraction methods (e.g., filtration, centrifugation, molecular weight cutoff separation, chromatography, or protein digestion) and analyzed by MALDI-TOF MS or LC/MS. MALDI-TOF MS allows for detection of intact high molecular-weight compounds, including peptides and proteins, up to 100-200 kDa. Limited compound separation is typically performed prior to analysis, resulting in a molecular fingerprint of the hundreds of compounds detected from the complex sample milieu. Proteins can also be purified from the samples, digested and analyzed by LC/MS, allowing for detection of the sample's unique proteomic fingerprint. Protein identification, if warranted, can be performed using tandem MS (MS/MS) techniques in which individual peptides are isolated and fragmented, for further sample characterization.

In addition to the kinds of sample constituents that would be analyzed by either GC/MS or LC/MS, there are a number of other constituents from each of the sample matrices that could require either wet chemistry or specialized instrumental methods. Some of the following might be applicable: conventional elemental analysis, ICP/MS, or AA; nutrient elements (N, P, K, Na, S); trace elements (As, Se, Ni, and Hg); elements interfering with microbial growth (Li, Ba, B, Br, I); neutron activation analysis—total element surveys, and/or semiquantitative determination of specific elements, in isolated fractions (inexpensive fingerprint of elemental makeup); Karl Fischer—water analysis; optical or NMR spectroscopy—Analysis of specific isolated and recovered organic constituents (if needed); and/or physical constants (less likely)—e.g., melting point, boiling point, optical rotation, density The results of these or, more likely, a smaller subset of these physical and chemical analyses will enable operators to predict reservoir effects of specific nutrient solutions injected into a reservoir for MEOR purposes. As the technology is adopted in declining and spent oil fields around the globe, chemical analytical methods and other measurement techniques will likely be refined and focused to provide maximum data quickly and at reduced costs. For example, if channel plugging is the primary goal in a particular watered-out reservoir, a series of quick tests for biomass and polymer/slime formation could evolve to provide the requisite information rapidly and inexpensively.

Some models predict that in situ MEOR production of surfactants or gases is likely to have little or no effect on enhancing oil recovery. Therefore, careful laboratory HTHP studies of actual bio-products produced by reservoir microorganisms in various nutrients and their ability to release trapped oil using a variety of petroleum-laboratory tests are warranted before large-scale reservoir nutrient injections are attempted. Promising bio-metabolites are tested in the laboratory using conventional industry test beds (e.g. surface tension tests, sand packs, and core floods) to quantify oil-release and channel-plugging potential before conducting field tests on selected oil reservoirs. To obtain sufficient quantities of bio-metabolites for these tests, larger HTHP growth chambers may be used.

Desirable reservoir microorganisms that can be cultured ex situ at ambient temperature and pressure are isolated in the laboratory from bottomhole samples. These are evaluated for possible future reservoir injection. Reservoir microbial communities are characterized via 16S ribosomal RNA gene sequencing, metagenomic sequencing, and bioinformatics analysis; results are used to significantly improve nutrient selection and to enhance MEOR processes over the long term.

The products of this novel process described herein include: (a) an annotated list of biometabolites produced by microorganisms in a targeted reservoir grown under reservoir conditions in a number of candidate nutrient media; (b) detailed chemical characterization of biometabolites; (c) results of culturing reservoir microorganisms under ambient conditions to isolate indigenous microbes that can be grown in fermenters and reinjected into the reservoir to further enhance oil release; (d) results of metagenomic studies and bioinformatics analysis to improve the process; (e) results of petroleum-laboratory tests to estimate channel-plugging and/or oil-releasing efficacy of various bio-metabolites; and (f) injection of optimum amounts of nutrient formulations at optimum concentrations and for optimum times in targeted reservoirs to enhance oil recovery and to avoid or to suppress souring and to avoid other undesirable or damaging effects to the reservoir, equipment, public health, and the environment.

In concert with reservoir engineers, the sub-surface volume of watered-out channels is calculated, and optimum amounts and concentrations of nutrients are injected into the reservoir to plug fingers, i.e. "thief zones". The well is capped for a period of time determined, in part, by results of HTHP experiments, and then secondary floods with water and/or $CO_2$, or other gases, or other treatments are initiated or resumed.

Results of petroleum-laboratory tests in sand packs, cores, etc. using actual bio-metabolites are used to estimate potential reservoir efficacy of various nutrient treatments. Sequential reservoir treatments are employed if indicated; e.g. MEOR-induced channel-plugging followed by nutrient injections to reach previously bypassed oil-bearing zones. Follow-up nutrient injections are targeted at producing desired bio-metabolites such as acids, gases, solvents, and surfactants as determined by petroleum geologists and reservoir engineers for the specific reservoir.

The described process technology may only release trapped oil, but can also be used to study any underground microbial community where pressure and temperature have to be maintained in the laboratory. Other important potential applications include, but are not limited to: biodegrading large, heavy-oil molecules in order to lower viscosity and improve production; In situ bio-upgrading of heavy oil and oil sands deposits; bio-converting trapped or uneconomical hydrocarbon deposits into more easily produced methane; and Uranium bioleaching in underground deposits If, for example, bacterial biomass and polymers are needed to block water channels, if acid production is required to dissolve carbonate rock, and if nitrates are needed to suppress sulfate-reducing (oil-souring) bacteria in a specific reservoir, treatment regimes can be custom-designed based on the HTHP-chamber culture results, and sand pack/core verification tests.

This invention will provide scientifically derived information directly applicable to target oil reservoirs that will enable operators to recover trapped oil, i.e. oil that cannot be recovered by conventional primary and secondary recovery techniques.

Additional applications for the method of the present invention are (a) $CO_2$ or water-after-gas $CO_2$ floods following channel plugging; (b) producing acid in carbonate reservoirs to dissolve reservoir rock thereby increasing permeability and porosity; (c) co-producing solvents and surfactants to lower interfacial tension and reduce oil viscosity; and (d) production of $CO_2$ and other gases to repressurize reservoirs, and to cause viscosity reduction and swelling of oil.

Additional expansion of the applications include, but are not limited to (a) MEOR for heavy oil deposits; (b) biodegrading large, heavy-oil molecules in order to lower viscosity and improve production; (c) in situ bio-upgrading of heavy oil and oil sands deposits; and (d) bio-converting trapped or uneconomical hydrocarbon deposits into more easily produced methane.

From the foregoing it will be seen that this invention is one well adapted to attain all ends and objects hereinabove set forth together with the other advantages which are obvious and which are inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative, and not in a limiting sense.

The invention claimed is:

1. A method for releasing and recovering trapped oil from a subterranean light-crude oil reservoir of an oil well comprising the steps of:
   (a) identifying a subterranean light-crude oil reservoir;
   (b) obtaining a microbial community sample from the bottomhole of said reservoir, said sample is collected in the bottomhole of said reservoir and maintained at the bottomhole temperature and the bottomhole pressure while being brought to the surface of said reservoir;
   (c) transferring said sample obtained from said bottomhole to a reservoir simulator that is an anaerobic chamber, said sample being maintained under bottomhole temperature and pressure conditions that substantially mimic natural conditions of said reservoir;
   (d) testing said sample by incubating said sample in at least one candidate liquid nutrient substrate medium formulation in said reservoir simulator, said sample being maintained under bottomhole temperature and pressure conditions that substantially mimic natural conditions of said reservoir;

(e) determining a targeted treatment regime for said reservoir based on positive growth of said sample in said nutrient substrate medium formulation, said sample being maintained under bottomhole temperature and pressure conditions that substantially mimic natural conditions of said reservoir;

(f) injecting said reservoir with a nutrient substrate medium formulation that provided positive growth in step (e) to produce microbial biomass or microbial metabolic byproducts or a mixture thereof and thereby releasing trapped oil in said reservoir;

(g) monitoring said reservoir; and (h) extracting said trapped oil from said reservoir.

2. The method of claim 1 further comprising a second step of injecting said reservoir with said nutrient substrate medium formulation that provided positive growth in step (e).

3. The method of claim 1 wherein said determining step further comprises the step of developing a substantially ideal treatment formulation including compounds selected from the group consisting of nutrients, salts, growth factors, suppressants, and combinations thereof.

4. The method of claim 1 wherein said injecting step further comprises injecting said nutrient following fishbone drilling.

5. The method of claim 1 wherein said nutrient substrate medium formulation contains a nutrient selected from molasses, fertilizer, paper/pulp waste, sugar beet waste, brewery waste, or feedlot waste.

6. The method of claim 1 wherein said nutrient substrate medium formulation includes at least one targeted nutrient.

7. The method of claim 6 wherein said nutrient present in said nutrient substrate medium formulation produces at least one targeted product or metabolic byproduct and said targeted product or metabolic byproduct is selected from the group consisting of acids, biomass, gases, solvents, surfactants, polymers, and mixtures thereof.

8. The method of claim 7 wherein said solvents are selected from the group consisting of alcohols, acetone, aldehydes, ketones, and mixtures thereof.

9. The method of claim 7 wherein said surfactants are selected from the group consisting of carboxylic acids, amines, heterocyclic compounds, amino acids, peptides, esters, poly-anionic lipids, and mixtures thereof.

10. The method of claim 7 wherein said gas is selected from the group consisting of carbon dioxide, methane, hydrogen, hydrogen sulfide, and mixtures thereof.

11. A method for releasing trapped light-crude oil in a subterranean light-crude oil reservoir of an oil well comprising the steps of:

(a) identifying a subterranean light-crude oil reservoir;

(b) obtaining a sample of a microbial community from the bottomhole of said reservoir, said sample is collected in the bottomhole of said reservoir and maintained at the bottomhole temperature and the bottomhole pressure while being brought to the surface of said reservoir;

(c) transferring said sample to a transport canister, said sample being maintained under bottomhole temperature and pressure conditions that substantially mimic natural conditions of said reservoir;

(d) transferring said sample from said transport canister to a reservoir simulator that is an anaerobic chamber, said sample being maintained under bottomhole temperature and pressure conditions that substantially mimic natural conditions of said reservoir;

(e) testing said sample by incubating said sample in at least one candidate liquid nutrient substrate medium formulation in said reservoir simulator, said sample being maintained under bottomhole temperature and pressure conditions that substantially mimic natural conditions of said reservoir;

(f) developing a targeted treatment regime based on test results produced from said testing, wherein said targeted treatment regime includes at least one target nutrient substrate medium formulation, said sample being maintained under bottomhole temperature and pressure conditions that substantially mimic natural conditions of said reservoir;

(g) performing said treatment regime in said reservoir of (a) to produce microbial biomass or microbial metabolic byproducts or a mixture thereof and thereby releasing trapped light-crude oil in said reservoir; and extracting said released light-crude oil from said reservoir.

12. The method of claim 11 wherein said targeted treatment regime further includes developing a substantially ideal formulation of nutrients, salts, growth factors, suppressants, and combinations thereof.

13. The method of claim 11 wherein said target nutrient substrate medium formulation contains a nutrient selected from molasses, fertilizer, paper/pulp waste, sugar beet waste, brewery waste, or feedlot waste.

14. The method of claim 11 wherein said target nutrient substrate medium formulation includes at least one targeted nutrient that produces at least one targeted microbial product or metabolic by product.

15. The method of claim 14 wherein said microbial product or metabolic byproduct is selected from the group consisting of acids, biomass, gases, solvents, surfactants, polymers, and mixtures thereof.

16. The method of claim 15 wherein said solvents are selected from the group consisting of alcohols, acetone, aldehydes, ketones, and mixtures thereof.

17. The method of claim 15 wherein said surfactants are selected from the group consisting of carboxylic acids, amines, heterocyclic compounds, amino acids, peptides, esters, poly-anionic lipids, and mixtures thereof.

18. The method of claim 15 wherein said gas is selected from the group consisting of carbon dioxide, methane, hydrogen, hydrogen sulfide and mixtures thereof.

* * * * *